United States Patent [19]

Kaemmerer

[11] 4,325,368
[45] Apr. 20, 1982

[54] INFUSION DEVICE

[75] Inventor: Erich Kaemmerer, Steinhagen, Fed. Rep. of Germany

[73] Assignee: Ingrid Bernard, Steinhagen, Fed. Rep. of Germany

[21] Appl. No.: 103,476

[22] Filed: Dec. 14, 1979

[30] Foreign Application Priority Data

Dec. 16, 1978 [DE] Fed. Rep. of Germany ....... 2854392
Feb. 26, 1979 [DE] Fed. Rep. of Germany ....... 2907479
Oct. 22, 1979 [DE] Fed. Rep. of Germany ....... 2943586

[51] Int. Cl.³ .......................... A61M 5/14; A61M 5/16
[52] U.S. Cl. ............................. 128/214 R; 128/214 C; 128/214.2; 128/214 G; 128/272.1; 128/272.3; 222/129; 215/247; 215/249; 215/DIG. 3; 215/DIG. 8
[58] Field of Search ........... 128/214 G, 214 C, 214 R, 128/214.2, 272, 272.1, 272.3; 222/129; 215/355, 309, 249, 247, DIG. 3, DIG. 8

[56] References Cited

U.S. PATENT DOCUMENTS

| | | | |
|---|---|---|---|
| 2,168,270 | 8/1939 | Paisley et al. ..................... | 128/214 C |
| 2,426,733 | 9/1947 | Gee ................................. | 128/214 C |
| 2,433,242 | 12/1947 | Shaw ............................... | 128/214 C |
| 2,438,906 | 4/1948 | Elsas et al. . | |
| 2,847,007 | 8/1958 | Fox ................................. | 128/214.2 |
| 2,911,123 | 11/1959 | Saccomanno . | |
| 3,034,504 | 5/1962 | Winsor et al. .................... | 128/214.2 |
| 3,217,711 | 11/1965 | Pecina et al. ..................... | 128/214 C |
| 3,347,420 | 10/1967 | Donoghue ........................ | 222/129 |
| 3,670,728 | 6/1972 | Dabney . | |
| 3,727,800 | 4/1973 | Santos .............................. | 222/129 |
| 4,000,740 | 1/1977 | Mittleman ........................ | 128/214 R |
| 4,005,710 | 2/1977 | Zeddies et al. ................... | 128/214 R |
| 4,048,995 | 9/1977 | Mittleman ........................ | 128/214 R |
| 4,048,996 | 9/1977 | Mittleman et al. ............... | 128/214 R |
| 4,195,631 | 1/1980 | Baucom ........................... | 128/214 R |
| 4,200,095 | 4/1980 | Reti ................................. | 128/214 C |

FOREIGN PATENT DOCUMENTS

| | | | |
|---|---|---|---|
| 366638 | 6/1923 | Fed. Rep. of Germany . | |
| 827537 | 12/1951 | Fed. Rep. of Germany . | |
| 915731 | 6/1954 | Fed. Rep. of Germany . | |
| 925373 | 2/1955 | Fed. Rep. of Germany . | |
| 966701 | 9/1957 | Fed. Rep. of Germany ... | 128/214.2 |
| 1039193 | 9/1958 | Fed. Rep. of Germany . | |
| 2048394 | 9/1972 | Fed. Rep. of Germany . | |
| 2612518 | 10/1976 | Fed. Rep. of Germany . | |
| 7719528 | 3/1978 | Fed. Rep. of Germany . | |
| 1224268 | 2/1959 | France ............................. | 128/214 C |
| 2003357 | 11/1969 | France . | |
| 854163 | 11/1960 | United Kingdom . | |

Primary Examiner—Robert W. Michell
Assistant Examiner—Nancy A. B. Swisher
Attorney, Agent, or Firm—Schwartz, Jeffery, Schwaab, Mack, Blumenthal & Koch

[57] ABSTRACT

An infusion device for medical purposes is described, comprising a container (10) with at least two chambers (14, 16), with their openings (20, 22) closable by means of sealing stoppers, in particular by a common stopper (12). The sealing stopper has a cavity (34) in the area of the opening (20) of the first chamber (14) which communicates with the second chamber (16). A cannula (42) may be pierced through the stopper (12) in the area of the opening (20) of the first chamber (14) and can simultaneously receive infusional solutions from the two chambers through two orifices (44, 46) spaced longitudinally from one another. The connection between the cavity (34, 40) in the stopper (12) may be established in one embodiment by means of a connecting cannula (56) with orifices (58, 60).

17 Claims, 13 Drawing Figures

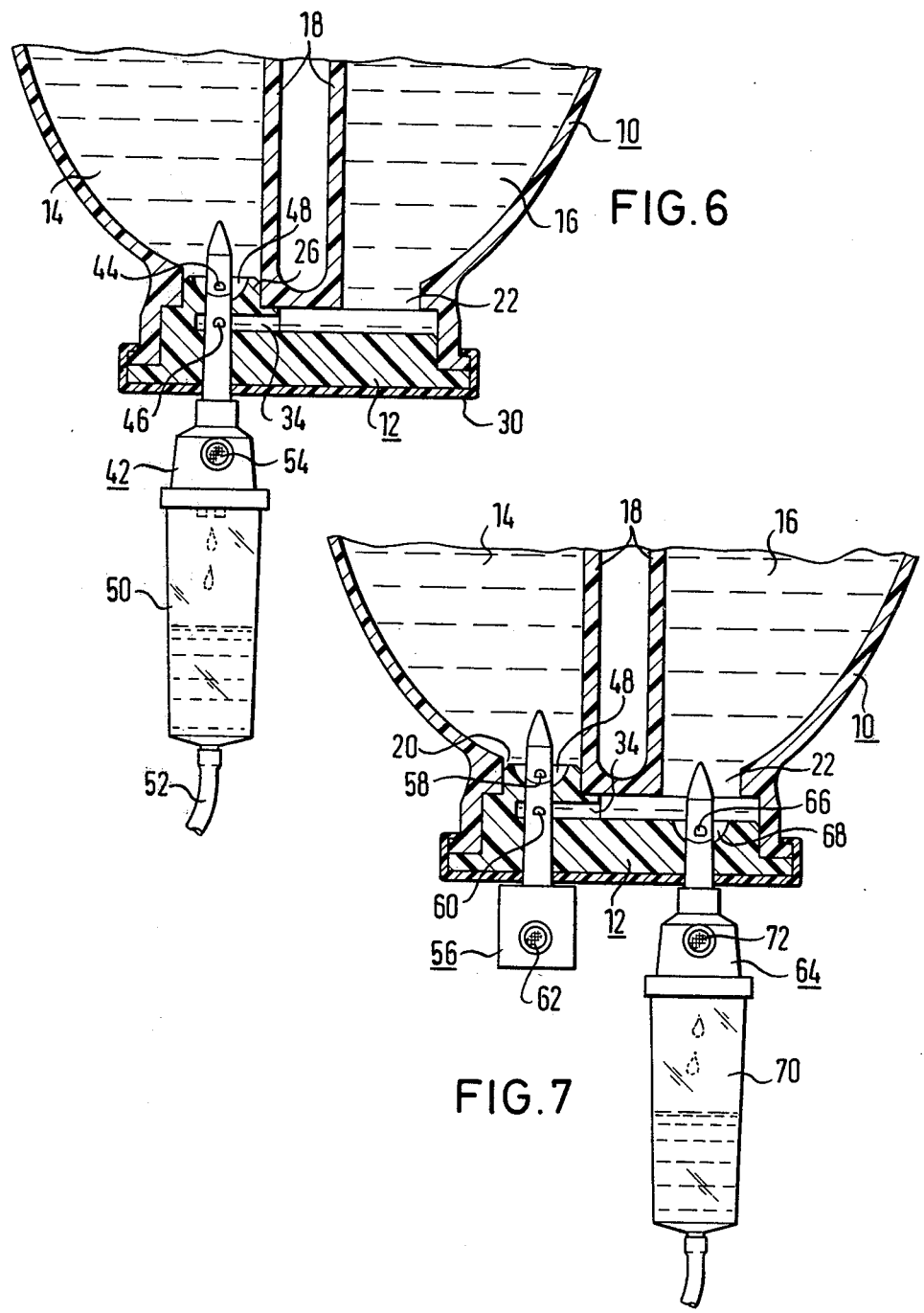

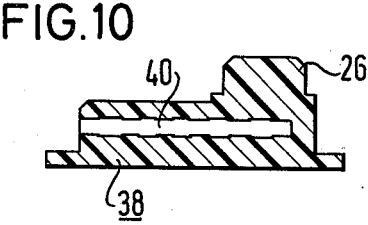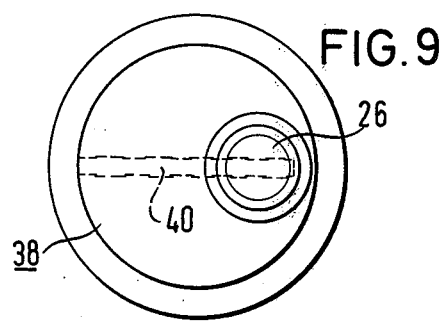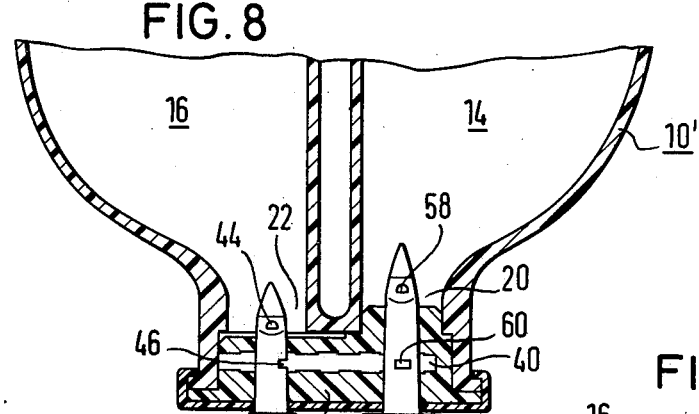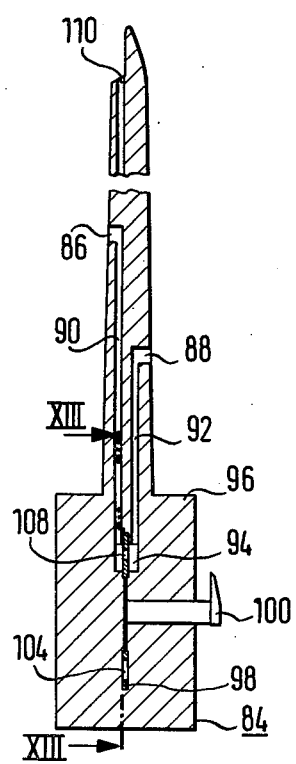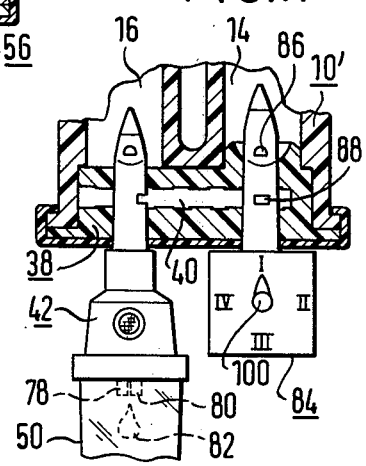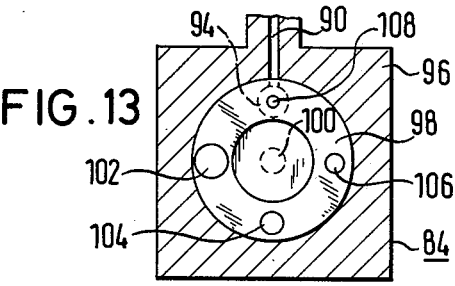

INFUSION DEVICE

BACKGROUND OF THE INVENTION

The present invention relates to an infusion device with a container having an opening at its bottom side in the operational position, sealable by means of a stopper, for the containment of an infusional solution, and a cannula penetrating the sealing stopper.

Infusion devices of this type with containers in the form of bags or bottles are known in different forms. The cannula is made to pierce the stopper, which consists mostly of rubber or a synthetic material, only at the time of use, but the present description will be based on the operational position of the infusion device, wherein the container is suspended with the stopper pointing downward and the cannula piercing the stopper.

In the practice of medicine, it is often necessary to administer several preparations simultaneously, possibly in different proportional amounts. It is therefore frequently necessary to use several containers of such different preparations, connect them by means of conduits and administer the medications in the form of a mixture. The presence of several containers with their corresponding connecting lines leads, however, to a confusing system which is not only inconvenient to handle, but makes erroneous interchanges possible.

In some cases it is possible to provide non-physiological mixed preparations in a single container; but in some instances, for example, physiologically metastable fat and glucose components, the preparations cannot be integrated and the dosage of proportional amounts of the components is not feasible.

SUMMARY OF THE INVENTION

It is therefore the object of the present invention to provide an infusion device of the above-described type which makes it possible to simultaneously administer at least two preparations in a simple manner.

In order to attain this object, the infusion device of the invention is characterized in that the container has at least two separate chambers, that the opening of a first chamber is sealed by a stopper having at least one internal cavity, that the cavity intersects the path of the cannula and is in communication with a second chamber, and that the cannula has orifices opening into the first chamber and the cavity, respectively.

The sealing stopper according to the invention, sealing the first chamber and simultaneously providing a connection to the second chamber by means of its internal cavity, makes it possible to engage both chambers simultaneously with the aid of a cannula having two orifices spaced with respect to each other in the longitudinal direction. This effect of the combination of a stopper and a cannula may be exploited in a variety of manners, as shall be described in detail hereinafter, but it is not restricted to two chambers and may be applied to a larger number of chambers.

In a first preferred embodiment of the invention, only a single cannula is provided, representing an outlet cannula having two interior channels, the channels being connected, on the one hand, with the cavity by means of separate orifices and, on the other hand, with the first chamber. These channels thus make it possible to discharge the infusional solution simultaneously from both chambers. Two addtional ventilation channels in the cannula effect an equalization of pressures in the two chambers.

In a further preferred embodiment of the invention, an additional connecting cannula is provided which connects the first chamber with the cavity and also contains a ventilation channel for the first chamber. In this manner, the solution from the first chamber passes by way of the cavity into the second chamber, and is intermixed at the bottom of the second chamber, directly above the corresponding sealing stopper, with the other solution. The mixture effected in this fashion may be discharged through a cannula with an inlet orifice.

In another embodiment of the invention, representing in a certain sense a combination of the first and the second embodiments, an outlet cannula with two inlet orifices takes infusional solutions from the first chamber and the cavity, while the cavity is interconnected with another cavity in a stopper for the second chamber, with the latter cavity being capable of communication with the second chamber by means of a connecting cannula.

The use of an additional connecting cannula makes it possible to insert in the connecting line of the connecting cannula a metering valve, so that the proportion of amounts of the two solutions may be regulated, which may be required in particular in the case of solutions having differing viscosities or differing specific gravities.

The outlet cannula may be integrally connected with a mixing vessel with which the outlet channels communicate. Preferably, the outlet channels protrude from above into the mixing vessel with a tubular section serving as a drip end, with the drip ends being arranged so closely adjacent one another that a common drop is formed, which then drops to the bottom of the mixing vessel.

Further details of the invention are found in the dependent claims.

Preferred embodiments of the invention are explained in more detail below with reference to the accompanying drawings.

BRIEF DESCRIPTION OF THE DRAWINGS

FIG. 6 shows a partial view of a container with a stopper and a cannula according to one embodiment of the invention;

FIG. 7 shows an embodiment of the invention with two cannulas;

FIG. 8 shows another embodiment of the invention with two cannulas;

FIGS. 9 and 10 show in top view and in section the sealing stopper according to FIG. 8;

FIG. 11 shows a further embodiment, partially coinciding with that of FIG. 8;

FIG. 12 is a vertical section through a connecting cannula according to FIG. 11; and FIG. 13 is a partial section along lines 13—13 in FIG. 12.

DETAILED DESCRIPTION OF PREFERRED EMBODIMENTS

Figure 1:
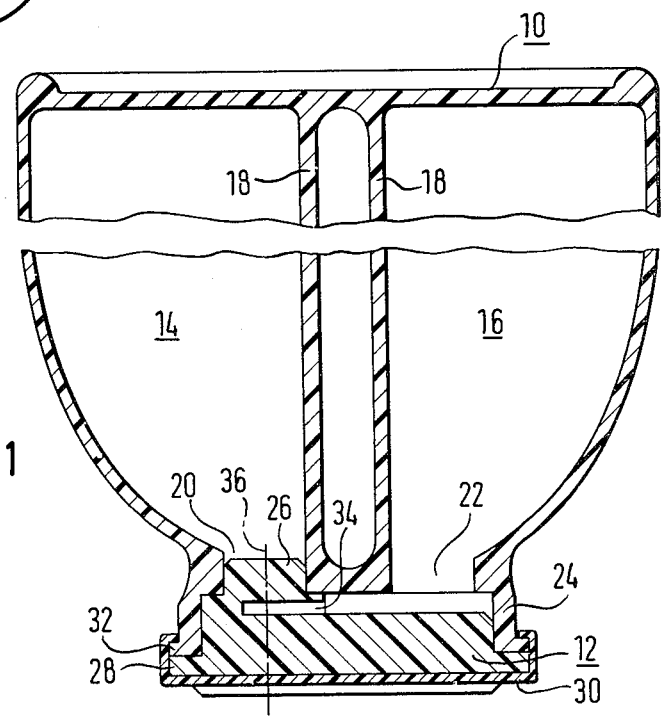
FIG. 1 is a vertical, partially interrupted section through a container with a sealing stopper.

FIG. 1 shows a container 10 with a sealing stopper 12 in the position that may be designated the operational position and in which the stopper is located on the underside of the container. For the purpose of filling the infusional solution in the first and second chambers 14, 16, the container 10 is placed in the inverted position. Between the chambers 14, 16 there is a separating wall 18, designed for reasons of production technology with a double wall. The overall shape of the container is immaterial. The container may be made of glass or particularly of a synthetic material and may be a bag.

Figure 2:
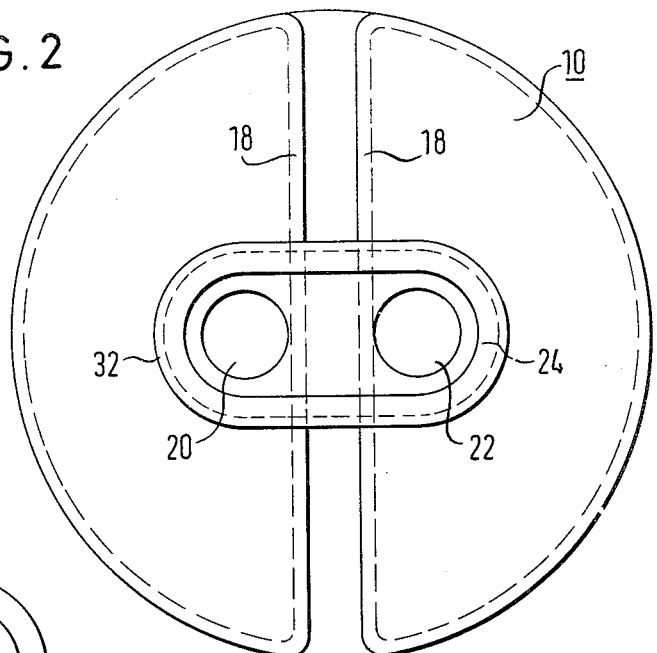
FIG. 2 is a bottom view of the container of FIG. 1, without the stopper.
Figure 3:
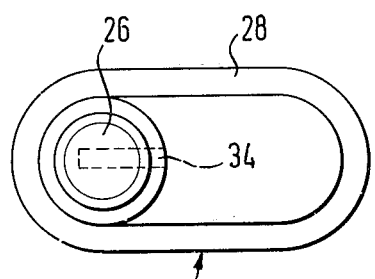
FIG. 3 shows a top view of a sealing stopper for covering both chamber openings.

The chambers 14, 16 have orifices 20, 22 located in accordance with FIGS. 1 and 2 adjacent to each other and in the same plane; they are surrounded by a common rim 24 protruding from the plane of the orifices 20, 22. The circumferential rim 24 serves to receive a common sealing stopper 12.

The sealing stopper 12 is elongated and semicircularly rounded about the orifices 20 and 22, and is provided with an outwardly protruding flange 28, which coveringly engages the rim 24. A holding cap 30 engages an outwardly protruding projection 32 of the rim 24 from behind and secures the stopper 12 within the rim 24.

In order to provide reliable separation of the chambers 14 and 16 from each other, a bung-like projection 26 extends from the stopper 12, having a circular cross section in the example shown and tightly closing the orifice 20. Within this bung-like projection 26 there is a cavity 34 in the form of a channel, entering the bung-like projection 26 from the right in FIG. 1, i.e., from the direction of the second chamber 16.

A stopper of this type makes it possible to introduce in the area of the orifice 20 of the first chamber 14, i.e., approximately along the dash-dot line 36, a cannula which, when provided with inlet orifices located at a suitable distance from each other, communicates simultaneously with the contents of both chambers 14, 16, as shall be explained in more detail below.

Figure 4:
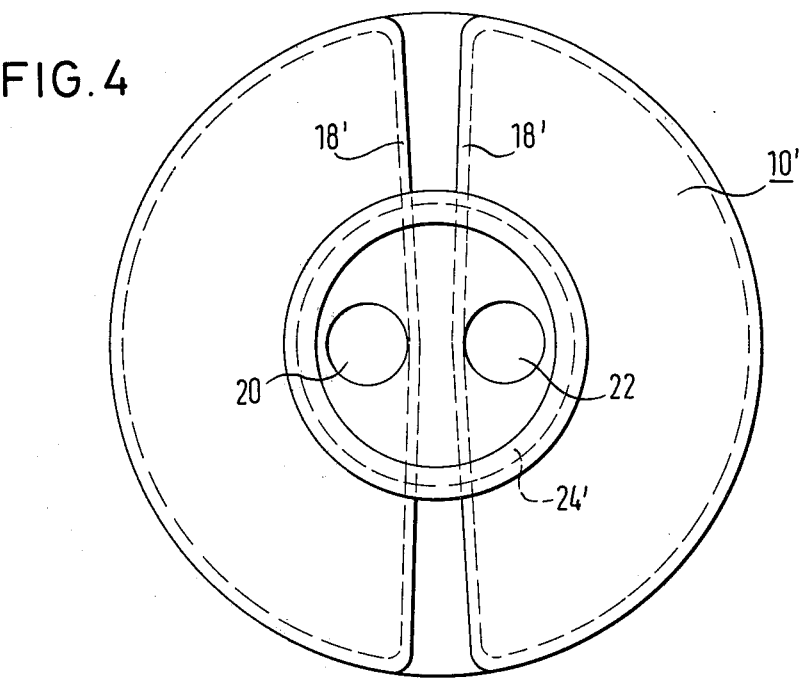
FIG. 4 shows a bottom view of a modified form of a container.

FIG. 4 shows a bottom-view of another container 10'. This container 10' differs from the container 10 of FIG. 2 essentially in that the two wall surfaces of the separating wall 18' between the chambers are slightly obliquely divergent toward both sides; this may be required for reasons of production technology. In addition, the rim 24' surrounding the orifices 20 and 22 is circular.

Figure 5:
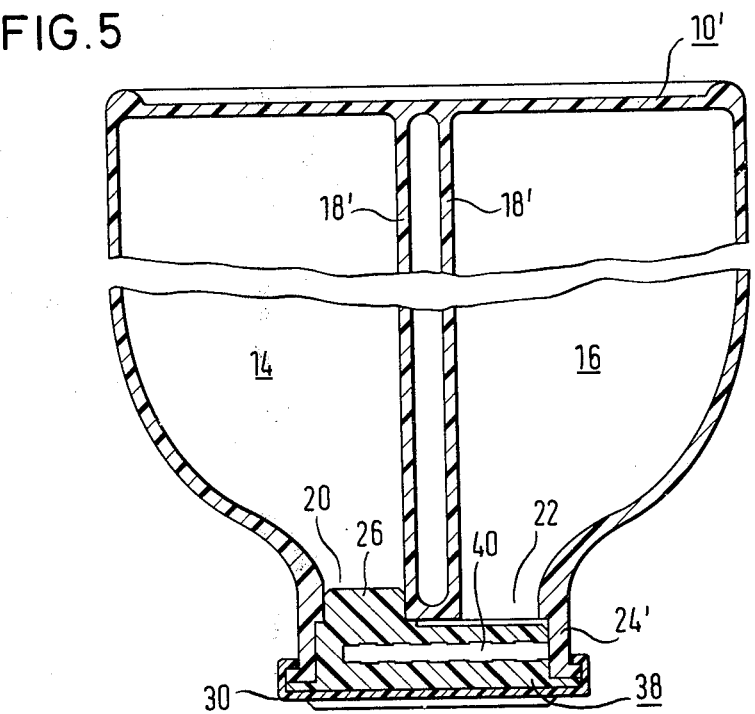
FIG. 5 is a vertical, partially interrupted section corresponding to FIG. 4.

Correspondingly, the stopper 38 shown in FIG. 5 also has a circular circumference. In addition, the manner of securing the stopper 38 within the rim 24' is similar to the solution described above in connection with FIG. 1, so that further explanation is unnecessary. As in the above-described embodiment, the stopper 38 has beneath the bung-like projection 26 which enters the orifice 20 of the first chamber 14, a cavity designated 40 in the present case which, however, in this case extends to the right in FIG. 5 to the rim 24' and does not open directly into the second chamber 16. The use of this stopper 38 will also be explained in more detail below.

FIG. 6 is largely similar to FIG. 1, but additionally has a cannula 42, which in this case represents an outlet cannula for the removal of infusional solutions from chambers 14 and 16. According to FIG. 6, the cannula 42 has orifices 44 and 46 longitudinally spaced from one another, the orifices being inter-connected with separate channels, not shown, inside the cannula, with one of them opening into the cavity 34 and the other into a trough 48 in the bung-like projection 26. The two outlet channels, not shown, extend to the upper side of a mixing vessel 50, which is integrated with the cannula and preferably transparent, and drip from there, as indicated in FIG. 6. From the bottom of the mixing vessel 50 a common infusion line 52 emanates, through which the mixed solution may be administered.

To equalize the pressure in the chambers 14, 16 while the infusional solution is running out, the cannula 42 has an air filter 54 outside the stopper 12, which communicates by way of ventilating channels, not shown, with the cavity 34 on one side and with the chamber 14 on the other and serves to admit air into the chambers.

The container 10 and the stopper 12 according to FIG. 7 are entirely similar to the corresponding parts of FIG. 6, so that no further explanation is necessary. In contrast to FIG. 6, a further cannula 56 is provided in the embodiment of FIG. 7, serving to connect the first chamber 14 and the cavity 34. Correspondingly, the connecting cannula 56 has two orifices 58 and 60 longitudinally spaced from one another and in communication with one another through a connecting channel, not shown, the orifices opening into the chamber 14 on one side and into the cavity 34 on the other. An air filter 62 on the connecting cannula 56 outside the stopper 12 communicates with a ventilation channel, not shown, admitting air into the first chamber 14.

A further cannula 64 in the form of an outlet cannula penetrates the stopper 12 in the area of the orifice 22 of the second chamber 10 and has an orifice 66 which opens into a trough 68 on the interior side of the stopper. At the underside of the cannula 64 there is again a mixing vessel 70. An air filter 72 serves to admit air into the chamber 16 by way of a ventilation channel, not shown.

In this embodiment, initially communication is established by the connecting cannula 56 between the first chamber 14 and the cavity 34 and, thus, simultaneously with the second chamber 16. The infusional solution from the first chamber 14 thus arrives at the bottom of the second chamber 16 so that there a mixture of the two solutions is formed. The mixture is discharged through the outlet cannula 64.

FIG. 8 shows a container 10' with the stopper 38 according to FIG. 5, so that an explanation of parts already described is not necessary. In the representation of FIG. 8, in contrast to the foregoing embodiments, the first chamber 14 is on the right and the second chamber 16 on the left side, even though the designation as first and second chamber is arbitrary and the chambers are interchangeable in every respect.

A connecting cannula 56 is inserted in the orifice 20 of the first chamber 14, as explained in connection with FIG. 7. This connecting cannula has an orifice 58 within the chamber 14 and an orifice 60 within the cavity 40, which are interconnected by means of a connecting channel, not shown. An air filter 62 admits air into the first chamber 14.

In the region of the orifice 22 of the second chamber 16, an outlet cannula is pierced into the stopper 12; this cannula corresponds to the outlet cannula 42 of FIG. 6 and is thus explained using corresponding reference numerals. Orifices 44 and 46 open into the second chamber 16, on the one hand, and on the other hand, into the cavity 40 which extends into the region of the orifice 22.

Further, an air filter 54 is provided on the cannula 42, permitting the ventilation of the second chamber 16 through a ventilating channel, not shown.

Outlet channels within the cannula 42, not shown, emanate from the orifices 44, 46, forming within the mixing vessel 50 the drip end 74, 76 protruding vertically downwardly and from which the solution drips.

In this embodiment, initially a connection is established between the first chamber 14 and the cavity 40 by means of the connecting cannula 56. Thereupon, the two solutions may be taken simultaneously from the second chamber 16, on the one hand, and from the cavity 40, on the other, through the orifices 44 and 46 with the aid of the cannula 42.

The embodiment according to FIG. 11 is largely similar to that of FIG. 8 and therefore only the differences will be explained. It may be seen initially that in this case the drip ends, designated by 78 and 80, of the outlet channels within the mixing vessel 50 are located directly adjacent to each other, so that they form a common drop 82, which already represents a mixture of the two solutions.

Further, a connecting cannula 84 is shown, which corresponds extensively to the connecting cannula 56, but contains additionally a metering valve. By means of this metering valve, the discharge of the solution from the first chamber 14 into the cavity 40 and thus the mixing ratio of the two solutions may be regulated. According to FIG. 12, the orifices 86 and 88, which according to FIG. 11 are located within the first chamber 14 and the cavity 40, are connected with the channel sections 90 and 92, which extend within the cannula 84 parallel to one another and vertically downward and which communicate with one another at the lower end of the cannula 84, within the housing 96, by means of a channel section 94 perpendicular to the sections 90 and 92.

Within the housing 96, a circular perforated disk 98 is rotatably arranged, having orifices of various diameters, which may be shifted selectively into the channel section 94 by means of a rotating handle 100. The orifices 102, 104, 106, 108 of various diameters, are schematically shown in FIG. 13. According to FIG. 13, the orifice 108 with the smallest diameter is within the channel section 94, so that the perforated disk in this case permits only the minimum passage of the solution. Obviously, any other number of orifices may be provided.

FIG. 12 further shows a partial area of a ventilating channel 110, which is connected in a manner not shown with an air filter 54 shown, for example, in FIG. 8.

It can be seen from the various embodiments described above that these are merely exemplary of the invention. The essentials are merely the cannula having two orifices and a sealing stopper permitting the connection of the cannula with the contents of the two chambers through one orifice each. The stopper does not necessarily consist of a single piece for both orifices. Rather, separate stoppers may be provided for the two orifices, as long as one of the stoppers has an internal cavity, connected in a suitable manner, for example, by means of an opening in the separating wall between the chambers, with the other chamber.

Alternatively, it is also possible to provide the sealing stopper not directly at the orifices of the chambers, but as a valve system at the terminals of intermediate lines emanating from the chambers.

It is further obvious that a greater number of chambers may be combined, if a sealing stopper with cavities in different planes and a cannula with orifices located in these planes is used.

What is claimed is:

1. An infusion device which is adapted to receive a penetrating cannula for simultaneously infusing a plurality of liquids, comprising:

a container having an orifice on the side which is the underside in the operational position, at least first and second chambers therein for holding a plurality of infusion liquids and first and second openings connecting said first and second chambers with said orifice;

and a stopper member for inserting into said orifice and sealing said orifice as well as sealing said first and second openings from one another, said stopper member including therein a cavity which lies in the path of a penetrating cannula and which is adapted to provide codispensing communication between said first and second chambers upon insertion of a penetrating cannula for codispensing said plurality of infusion liquids.

2. An infusion device according to claim 1, wherein said cavity in said stopper member is normally in communication with said first chamber and is normally sealed from said second chamber but lies in the path of a penetrating cannula into said second chamber, whereupon by insertion of a penetrating cannula into said second chamber communication is achieved between said first and second chambers.

3. An infusion device according to claim 1, wherein said cavity in said stopper member is normally sealed from both said first and second chambers but lies in the path of a penetrating cannula into both of said chambers, whereupon communication is achieved between said first and second chambers by insertion of a penetrating cannula into both of said first and second chambers.

4. An infusion device according to claim 1, 2 or 3, further comprising a first penetrating cannula inserted through said stopper member into said second chamber and intersecting said cavity, said first cannula including a first aperture opening into said second chamber and a second aperture opening into said cavity.

5. An infusion device according to claim 4, wherein said first and second apertures are each connected with a separate passageway in said first cannula for separately codispensing said plurality of liquids.

6. An infusion device according to claim 4, wherein said first and second apertures are interconnected with each other, and wherein said device further comprises a second penetrating cannula inserted through said stopper member into said first chamber and intersecting said cavity, said second cannula including a first aperture opening into said cavity.

7. An infusion device according to claim 6, wherein said second cannula includes a second aperture opening into said first chamber and wherein said first and second apertures of said second cannula are each connected with a separate passageway in said second cannula for separately codispensing said plurality of liquids.

8. An infusion device according to claim 1, further comprising a metering valve interposed in the connecting channel connecting said first and second apertures in said first cannula.

9. An infusion device according to claim 8, wherein said metering valve comprises a perforated disk, rotatable in a plane perpendicular to the connecting channel, with orifices of different diameters, said orifices being displaceable selectively into the path of the connecting channel.

10. An infusion device according to claim 6, wherein said first and second cannulas include ventilation channels entering said first and second chambers.

11. An infusion device according to claim 10, wherein each said ventilation channel comprises an air filter.

12. An infusion device according to claim 6, further comprising a metering valve interposed in the connecting channel connecting said first and second apertures in said first cannula.

13. An infusion device according to claim 12, wherein said metering valve comprises a perforated disk, rotatable in a plane perpendicular to the connecting channel, with orifices of different diameters, said orifices being displaceable selectively into the path of the connecting channel.

14. An infusion device according to claim 4, wherein said first cannula includes a ventilation channel entering said second chamber.

15. An infusion device according to claim 14, wherein each said ventilation channel comprises an air filter.

16. An infusion device according to claim 1, wherein said openings of said chambers are arranged adjacent to each other and may be closed with a common stopper member, said stopper member having at least one bung-like projection for insertion into one of said openings.

17. An infusion device according to claim 16, wherein said openings are surrounded by a common rim projecting from the plane of the openings, said rim receiving the common stopper member.

* * * * *